United States Patent
Hansen et al.

(10) Patent No.: US 7,133,722 B2
(45) Date of Patent: Nov. 7, 2006

(54) DEVICE-TO-LEAD TERMINAL CONNECTOR FOR IMPLANTABLE TISSUE STIMULATORS

(75) Inventors: David J. Hansen, Oakdale, MN (US); Timothy Hillukka, Maple Grove, MN (US); Jason Sprain, Shoreview, MN (US); Robyn Mrozinski, Hugo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 338 days.

(21) Appl. No.: 10/748,426

(22) Filed: Dec. 30, 2003

(65) Prior Publication Data

US 2005/0149140 A1    Jul. 7, 2005

(51) Int. Cl.
*A61N 1/375*    (2006.01)
(52) U.S. Cl. .......................................... 607/37; 607/36
(58) Field of Classification Search .................. 607/37; 439/462
See application file for complete search history.

(56) References Cited

U.S. PATENT DOCUMENTS

| | | | |
|---|---|---|---|
| 4,860,750 A | * | 8/1989 | Frey et al. ..................... 607/37 |
| 5,383,914 A | | 1/1995 | O'Phelan |
| 5,413,595 A | * | 5/1995 | Stutz, Jr. ...................... 607/37 |
| 5,486,202 A | * | 1/1996 | Bradshaw ..................... 607/37 |
| 5,766,042 A | | 6/1998 | Ries et al. |
| 6,006,135 A | | 12/1999 | Kast et al. |
| 6,080,188 A | * | 6/2000 | Rowley et al. ............... 607/37 |

* cited by examiner

*Primary Examiner*—George R. Evanisko
*Assistant Examiner*—Michael Kahelin
(74) *Attorney, Agent, or Firm*—Thomas J. Nikolai; Nikolai & Mersereau, P.

(57) ABSTRACT

A device-to-lead terminal connector for an implantable medical device is designed to positively lock the proximal lead terminal within a lead bore formed in the connector of the implantable device. Rather than using a conventional setscrew locking arrangement, first and second latching members are insertable through side ports in the device connector that intersect with the lead bore and that contain an elastomeric sleeve. When the latching members are squeezed together, they cooperate to expand the elastomeric sleeve against the proximal lead terminal to press it into intimate electrical and mechanical engagement with a contact in the lead bore of the device connector. The need for a tool to effect locking of the lead terminal in place is dispensed with.

12 Claims, 5 Drawing Sheets

DEVICE-TO-LEAD TERMINAL CONNECTOR FOR IMPLANTABLE TISSUE STIMULATORS

BACKGROUND OF THE INVENTION

1. Field of the Invention

This invention relates generally to implantable medical devices for stimulating target tissue, and more particularly to, implantable pulse generators connecting to one or more elongated, electrode bearing leads and incorporating a locking mechanism for retaining a proximal end of the said lead in electrical and mechanical engagement with the input/output contacts of the pulse generator.

2. Discussion of the Prior Art

Dating back to the late 1950's and early 1960's, advances have been made in the treatment of patients through the application of electrical stimulation to target tissue from a pulse generator that is surgically implanted, subcutaneously or submuscularly, within a patient. A medical lead, comprising an elongated, flexible, insulating lead body and having surface electrodes thereon at a distal end and flexible conductors extending through the lead body for connecting the electrodes to a proximal terminal, is used to deliver electrical stimulation from the device to tissue abutting the electrodes and, in the case of cardiac rhythm management devices, to convey depolarization signals picked up by the electrodes back to the pulse generator.

In a typical prior art design, the proximal terminal of the medical lead comprises a rigid, straight pin having one or more electrical contacts disposed along its length. The pulse generator, in turn, has a molded plastic or epoxy connecter affixed to a hermetically sealed housing containing a battery power supply and electronic circuitry for delivering pulses in accordance with control signals provided by a microprocessor-based controller. The input and output nodes of the electronic circuitry are connected by feed-through wires that pass through suitable seals and connect to contact rings in a terminal receiving bore formed in the connector. The contact rings in the connector are adapted to mate with the electrical contacts of the lead terminal when the lead terminal is properly inserted and locked in place in the connector.

In the beginning, the implantable pulse generators were generally the size of a hockey puck. With improvements in circuit design and integrated circuitry, cardiac pacemakers and spinal cord stimulators are presently about the size of a silver dollar and about four times as thick. Efforts are still underway to further reduce the size and thickness of the implantable devices to render them less noticeable cosmetically. One design feature that has made it difficult to reduce the thickness dimension of such devices is the lead securing mechanism used in the header of the pulse generator.

In a typical prior art design, the lead locking mechanism comprises a block or blocks of metal disposed in the connector and having a longitudinal bore(s) for receiving the proximal end portion of the lead's proximal terminal therein. A threaded, transversely-extending bore that intersects with the longitudinal bore is also provided in the block for receiving a set screw. Once the proximal lead terminal is inserted into the longitudinal bore of the block comprising the locking mechanism, the setscrew is tightened down against the terminal in one or more locations. This forces the terminal pin into intimate contact with the wall of the longitudinal bore. Such a locking device mandates a connector whose thickness must be sufficient to contain the block of the locking member, the setscrew and a seal plug assembly used to prevent ingress of bodily fluids through the threaded bore. Such a construction typically drives a connector thickness of at least 7 mm. The prior art design also requires the use of a torquing tool to advance the setscrew.

It is also advantageous that one be able to replace a pulse generator without also having to replace the medical lead. Industry standards have been established for lead terminals in terms of their size (diameter and length), the location of contacts and location of insulation and seals. Therefore, any lead locking mechanism in a pulse generator should be such that it cooperates with a portion of the terminal that is in compliance with the standard, such as the proximal tip portion of the lead.

The present invention offers a lead lock mechanism that allows for a thinner connector than has heretofore been possible to achieve using setscrew technology. Moreover, the lead lock mechanism of the present invention does not require any special tools to effect locking. Also, the lead lock mechanism of the present invention is designed to accommodate any medical leads conforming to a given international standard.

SUMMARY OF THE INVENTION

The instant invention provides a tool-less connector for an implantable medical device. The device may include an implantable pulse generator contained within a hermetically sealed housing and that has a connector affixed to a predetermined surface of the housing. The header includes first and second side surfaces and a front surface. At least one longitudinally extending bore is formed inwardly from the front surface and is adapted to receive a proximal terminal of a medical lead therein. The proximal terminal of the lead has a conductive pin at a proximal end thereof. At least one electrical contact is disposed in the connector. It is positioned to cooperate with the conductive pin of the lead terminal when the proximal terminal of the lead is fully inserted into the longitudinal bore in the header. First and second side ports extend inwardly from the first and second side surfaces of the connector and the side ports intersect with the longitudinal bore at a location that is in general alignment with the electrical contact. An elastomeric tube is inserted through one of the first and second side ports. In accordance with the present invention, a first latch member is adapted to be inserted through the first side port. The first latch member includes a pair of bifurcated legs that extend into the lumen of the elastomeric tube. Completing the arrangement is a second latch member that is insertable through the second side port into the lumen of the elastomeric tube. The second latch member has a tapered wedge surface that is adapted to spread the bifurcated legs of the first latch member apart and thereby press the elastomeric tube against the conductive pin of the lead. The force applied is sufficient to hold that conductive pin in place against the electrical contact when the first and second latch members are squeezed together, such as by being pinched between the physician's thumb and forefinger.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
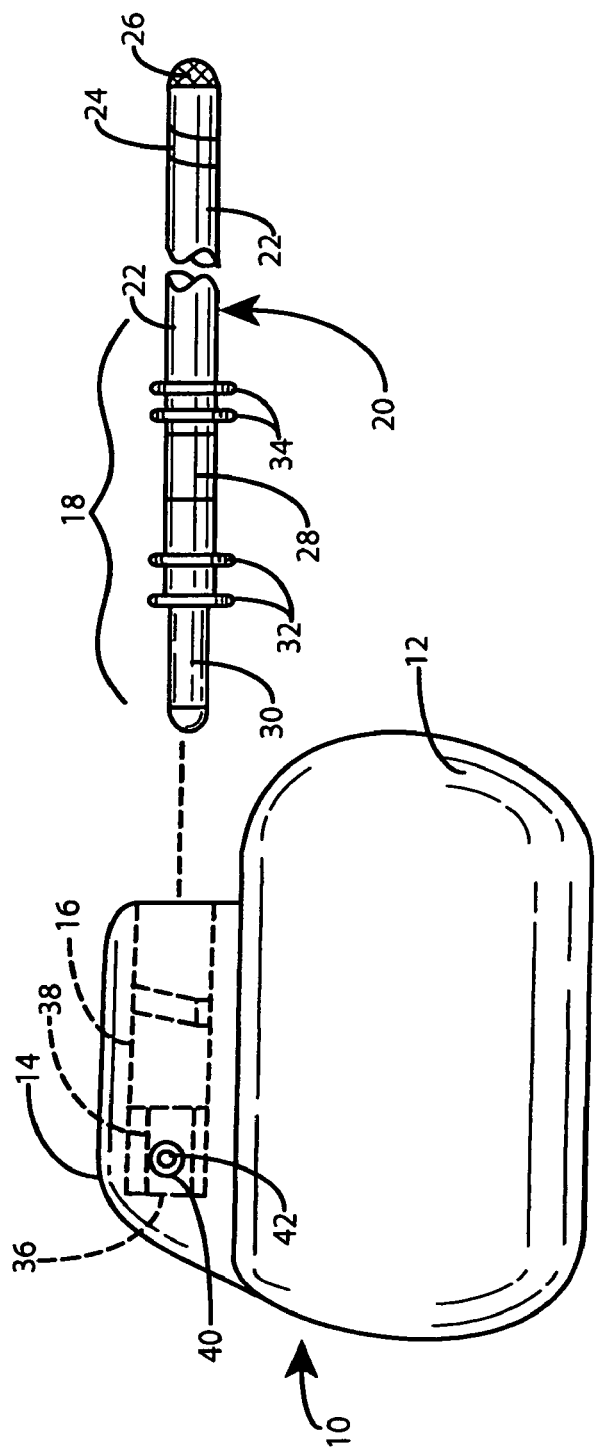
FIG. 1 is a side elevation of a prior art implantable tissue-stimulating device over which the present invention is an improvement.

Referring to FIG. 1, there is indicated generally by numeral 10 a prior art tissue stimulating device, such as a cardiac rhythm management device or a nerve stimulator. It is seen to comprise a hermetically sealed housing 12 which will typically contain a battery and electronic circuitry for producing pulses of preprogrammed amplitude, duration and repetition rate dictated by a microprocessor-based controller forming a part of the electronic circuit contained within the hermetically sealed housing 12. The tissue-stimulating device 10 has a molded plastic connector 14 affixed to it and formed longitudinally in the connector is a lead receiving bore 16 into which the terminal portion 18 of a medical lead 20 is inserted.

As is well known in the art, the lead 20 comprises an elongated, flexible, plastic lead body 22 having one or more electrodes, as at 24 and 26, proximate its distal end. These electrodes are connected by elongated flexible conductors (not shown) that extend through the lead body 24 and are insulated from one another. The conductors connect to contacts as at 28 and 30, disposed on the proximal terminal 18 of the lead. Sealing rings on the lead, as at 32 and 34, interface with the wall of the bore 16 to prevent ingress of body fluids into the bore of the connector 14.

In accordance with the prior art, the implantable device 10 will include a locking mechanism in the connector for preventing disengagement of the contact areas 28 and 30 on the lead terminal 18 from mating contacts contained in the bore 16. A typical prior art lead lock comprises a block of metal 36 having a longitudinal bore 38 formed therethrough, that bore being intersected by a transversely extending threaded bore 40. Fitted into the threaded bore 40 is a setscrew 42. An elastomeric plug is fitted into the bore 40, again to prevent ingress of body fluids into the interior of the connector. At the time of implant, the setscrew is tightened using a torquing tool inserted through the elastomeric plug so as to tightly press the contact 30 on the lead against the wall of the bore 38.

It can be appreciated from what has thus far been described that this prior art approach mandates a relatively wide connector, i.e., about 8 mm, in order to accommodate the locking block 36 a predetermined number of threads of the setscrew and a seal plug. Moreover, as mentioned, the implanting physician must be provided with an appropriate torquing tool, such as an Allen wrench, for tightening the setscrew.

Figure 2:
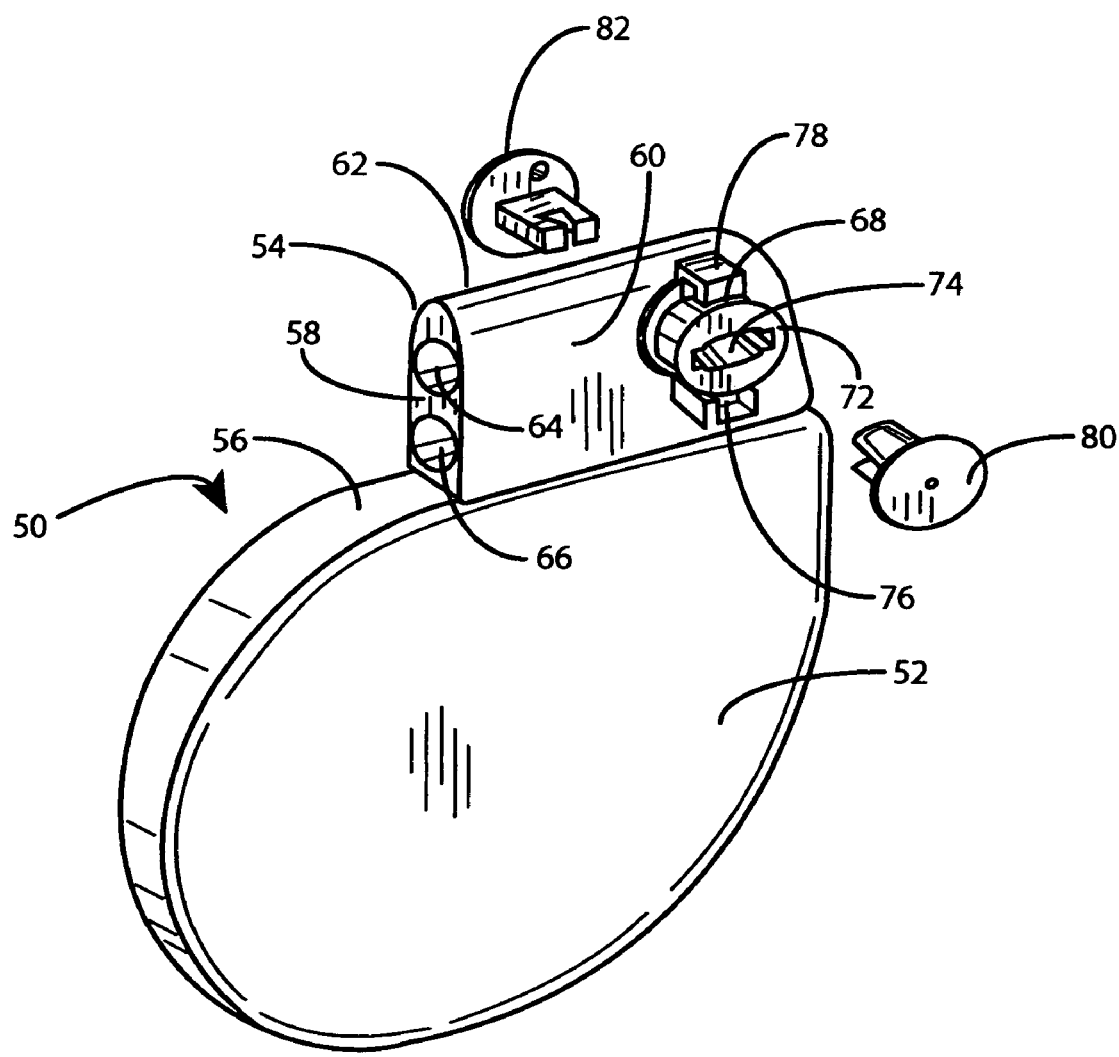
FIG. 2 is an isometric view of an implantable tissue stimulator device incorporating the tool-less lead locking mechanism of the present invention in an exploded form.

Referring next to FIG. 2, there is shown an implantable tissue-stimulating device incorporating the novel lead locking mechanism of the present invention. Again, the pulse generator 50 includes a hermetically sealed housing 52 having a molded plastic connector 54 affixed to a planar surface 56 of the housing. The connector 54 has a front surface 58 and opposed side surfaces 60 and 62. Formed inward from the front surface 58 are lead receiving bores 64 and 66 which, as in the prior art design, are adapted to receive the proximal terminal of a pair of medical leads therein.

A first side port 68 extends inwardly from the side surface 60 of the connector to intersect with the longitudinal bores 64 and 66. In a similar fashion, a second side port 70 (FIG. 6) is formed inwardly of the side surface 62 of the connector to also intersect with the longitudinal bores 64 and 66. An elastomeric tube or sleeve, preferably formed from silicon rubber and of one piece continuous construction is identified by numeral 72. It is inserted through one of the first and second side ports to be centered crosswise in the connector and the tube 72 includes a lumen 74. When the elastomeric tube is inserted in the manner shown in FIG. 2, its outer periphery does not appreciably occupy the bores 64 and 66.

With continued reference to FIG. 2, associated with each of the bores 64 and 66 is a metal contact. More particularly, a metal contact 76 is associated with the bore 66 and a metal contact 78 is provided in the bore 64. Each of the contacts 76 and 78 has a semicircular recess formed therein whose radius is only slightly larger than the radius of the terminal contact 30 on the medical lead 20 (FIG. 1). As such, upon insertion of the lead terminals into the longitudinal bores 64 and 66, the contact 30 of the lead terminal inserted into the bore 64 will fit into the semicircular recess of the contact 78 and slightly depress the elastomeric sleeve 72. Likewise, as a lead terminal is inserted into the bore 66, its contact 30 will fit into the semicircular recess of the contact 76 while again slightly compressing the elastomeric sleeve 72.

To lock the leads in place against their respective contacts 76–78 and thereby prevent the leads from coming loose in the connector, a first latching member 80 is inserted into the lumen 74 from the side 60 of the connector and a second latching member 82 is inserted into the lumen 74 of the sleeve from the side 62. Retention features on lumen 74, latching members 80 and 82, and on header 54 allow the device 50 to be shipped with 80 and 82 partially engaged. This minimizes any assembly by the physician. As will be explained in greater detail herein below, when the first and second latching members are squeezed together against the respective side surfaces 60 and 62, the elastomeric sleeve 72 is radially expanded to thereby firmly press the contacts 30 of the medical lead against the respective contacts 76 and 78 located in the connector. This provides electrical connection between the lead and connector. Additionally, the resulting frictional forces are such that the lead terminal contacts are able to remain in place even when substantial pulling forces are applied to the leads. Moreover, the elastomeric sleeve 72 forms a seal with the latching members 80, 82 and connector 54 to prevent ingress of body fluids into the interior of the header.

Figure 3:
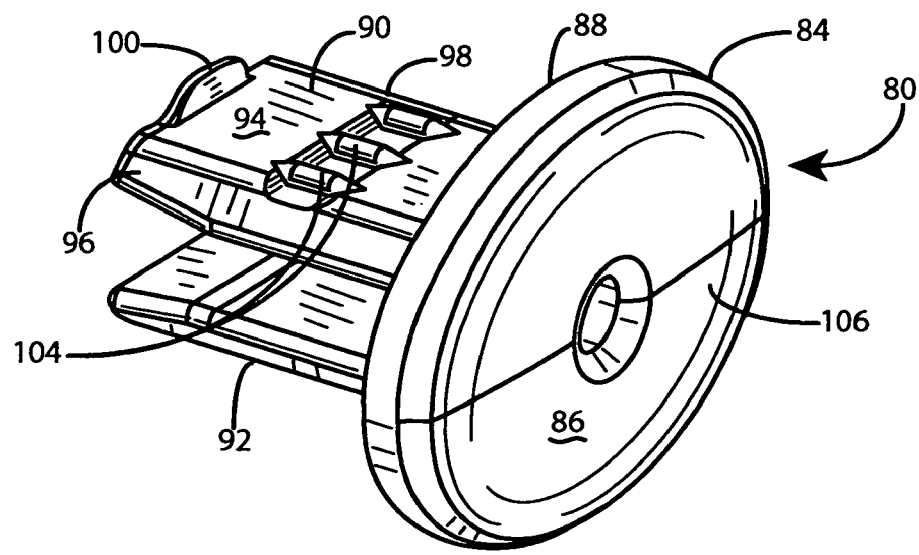
FIG. 3 is an isometric view of a first latch member shown in FIG. 2.
Figure 4:
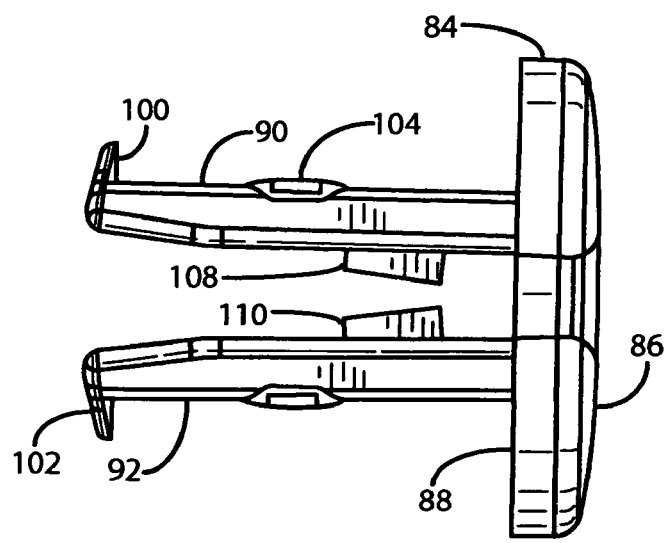
FIG. 4 is a side elevation of the first latch member of FIG. 3.

Referring next to FIG. 3, there is shown an isometric view of the first latching member 80 shown in FIG. 2. It is seen to comprise a molded plastic part having a head member 84 in the form of a oval disk with a slightly convex face 86 and generally flat base 88. Integrally formed with the head member 84 and projecting generally perpendicular from the base 88 are legs 90 and 92. The legs 90 and 92 have a somewhat flat outer surface 94 with radiused side edges 96 and 98. Projecting outward from the surfaces 94 at the end of each of the legs is a protuberance 100 and 102. Also rising from the surface 94 of each of the legs is a series of elongated knobs as at 104. An aperture 106 is formed through the thickness dimension of the head 84 at the center thereof and longitudinally aligned with this aperture and projecting inwardly from each of the legs 90 and 92 are latches 108 and 110 (FIG. 5).

Figure 5:
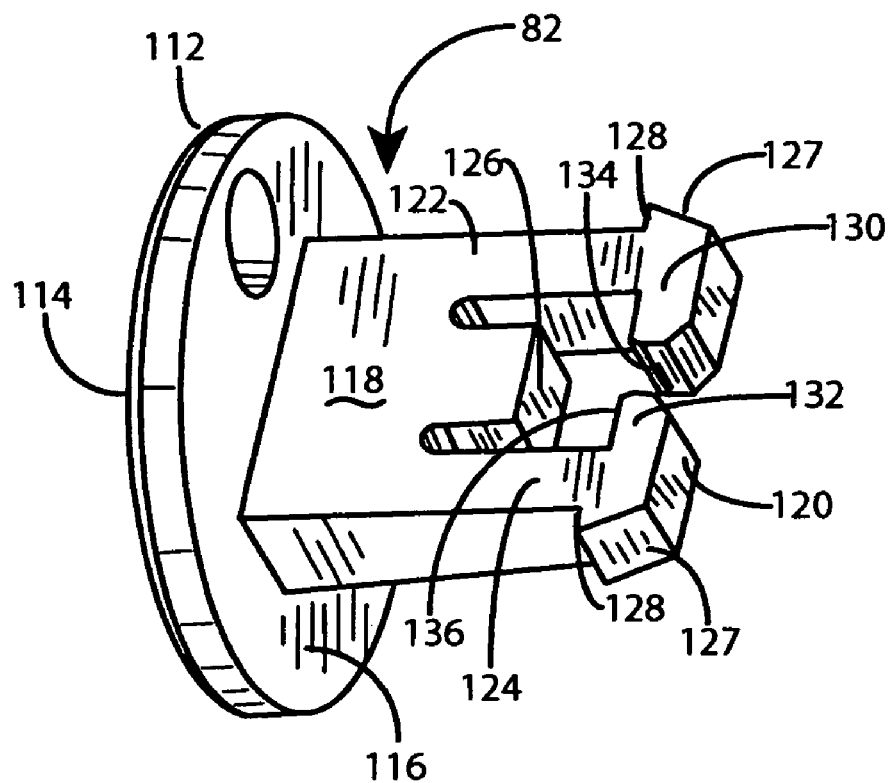
FIG. 5 is an isometric view of a second latch member shown in FIG. 2.

Turning next to FIG. 5, there is an isometric view of the second latching member 82. It, too, comprises a generally oval-shaped head member 112 having a slightly convex outer face 114 and a generally flat interface 116. Integrally molded with and projecting outwardly from the interface 116 is a wedge member 118 that tapers in thickness (from thicker to thinner) in progressing from the head 112 to the free ends of the wedge member 120. Formed inwardly from the free end 120 is a cut-out that defines first and second arms 122 and 124 that are spaced from one another and positioned on either side of a center post 126. Each of the arms 122 and 124 has a beveled surface 127 terminating in a shoulder 128 to form a barb. The cut-out in the wedge member 118 also defines inwardly projecting fingers 130 and 132 that are directed toward one another but separated by a gap. The fingers thereby result in the formation of latch surfaces 134 and 136.

Figure 6:
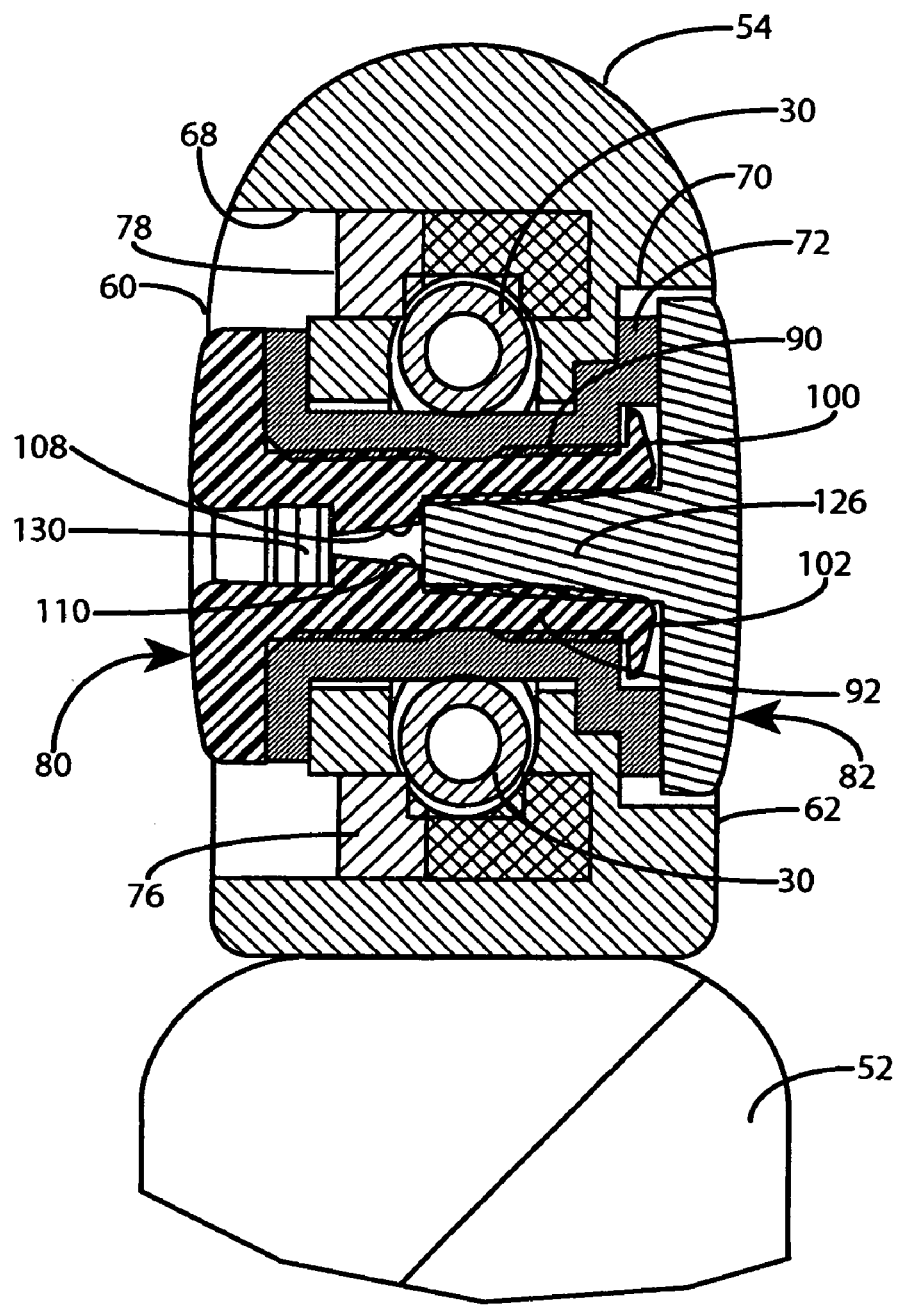
FIG. 6 is a greatly enlarged transverse cross-section taken through the header of the implantable tissue stimulator incorporating the novel lead locking mechanism of the present invention illustrating the locking engagement of the first and second latching members.

FIG. 6 is a transverse cross-section view taken through the locking mechanism with the latching members 80 and 82 fully engaged and latched. it can be seen that the wedge-shaped center post 126 serves to spread the legs 90 and 92 of the latching member 80 apart, thus compressing the elastomeric sleeve 72 against the lead terminals 30 to bring the lead terminals 30 in firm engagement with the contacts 76 and 78. The protuberances 100 and 102 of the latching member 80 engage a shoulder formed in the lumen 74 of the sleeve 72 and that the barbs on fingers 130 and 132 mate with latches 108 and 110 of the member 80, inhibiting separation of the latching members. The two pieces 80 and 82 may then be dismayed by a physician by inserting a tool or common torque wrench through orifice 106 in member 80. During insertion of the tool or torque wrench, tabs 130 and 132 are separated by the tool and flexing of legs 122 and 124. With the locking tabs spread apart, further insertion of the tool brings it into contact with center post 126, thus allowing the user to push out latching member 82 and disengage the latch. Barbs 128 and protuberances 100 and 102 prevent the latching mechanisms 80 and 82, respectively, from coming out.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A device connector-to-lead terminal connector for an implantable medical device comprising:
   (a) an implantable pulse generator contained within a hermetically sealed housing;
   (b) a device connector affixed to a predetermined surface of said housing, the device connector having first and second side surfaces and a front surface and having at least one longitudinally extending bore formed inwardly from the front surface adapted to receive a proximal terminal of a medical lead therein, the proximal terminal including a conductive pin at a proximal end of the terminal;
   (c) an electrical contact disposed in the device connector and positioned to cooperate with the conductive pin when the proximal terminal of the medical lead is fully inserted into the longitudinal bore;
   (d) said device connector having first and second side ports extending inwardly from said first and second side surfaces to intersect with the longitudinal bore in alignment with the contact;
   (e) an elastomeric tube inserted through one of the first and second side ports and oriented crosswise to the longitudinally extending bore, the elastomeric tube having a central lumen and a radial flange on opposed ends of said tube;
   (f) a first latch member adapted to be inserted through the first side port, the first latch member including a pair of bifurcated legs extending into said lumen; and
   (g) a second latch member insertable through the second side port into said lumen and having a tapered wedge surface adapted to spread the bifurcated legs of the first latch member apart and press the elastomeric tube against the conductive pin with a force sufficient to hold the conductive pin in place against the electrical contact when the first and second latch members are squeezed together, the radial flanges forming moisture impervious seals between the first and second side surfaces of the device connector and the first and second latch members.

2. The device connector-to-lead terminal connector as in claim 1 wherein the first latch member includes a barb on each of the pair of bifurcated legs and the elastomeric tube includes a shoulder proximate one end thereof for receiving said barbs when the first latch member is assembled into the device connector.

3. The device connector-to-lead terminal connector as in claim 1 wherein the first latch member comprises a generally flat head with said pair of legs integrally formed therewith and extending generally perpendicularly therefrom.

4. The device connector-to-lead terminal connector as in claim 1 wherein said second latch member comprises a generally flat head member with said tapered wedge surface integrally formed therewith and extending generally perpendicularly therefrom.

5. The device connector-to-lead terminal connector as in claim 2 wherein said first latch member and said second latch member interlock with one another upon their being squeezed together.

6. The device connector-to-lead terminal connector as in claim 1 wherein the first and second latching members, when inserted into the first and second side ports are located in the device connector to cooperate with a predetermined portion of the conductive pin that is defined by an international standard for selected medical leads, bringing the conductive pin into zero clearance fit with the electrical contact.

7. In an implantable medical device, said device having an implantable pulse generator contained within a hermetically sealed housing, a device connector affixed to a predetermined surface of said housing, the device connector having first and second side surfaces and a front surface and having at least one longitudinally extending bore formed inwardly from the front surface adapted to receive a proximal terminal of a medical lead therein, the proximal terminal including a conductive pin at a proximal end of the terminal, and an electrical contact disposed in the device connector and positioned to cooperate with the conductive pin when the proximal terminal of the medical lead is fully inserted into the longitudinal bore, an improved lead terminal connector for securing the lead terminal in place, comprising:
- (a) first and second side ports extending inwardly from said first and second side surfaces of the header to intersect with the longitudinal bore and in general alignment with the electrical contact;
- (b) an elastomeric tube inserted through one of the first and second side ports, the elastomeric tube having first and second radial flanges on opposed ends thereof and a central lumen oriented crosswise to said longitudinal bore;
- (c) a first latch member adapted to be inserted through the first side port, the first latch member including a pair of bifurcated legs extending into said lumen; and
- (d) a second latch member insertable through the second side port into said lumen and having a tapered wedge surface adapted to spread the bifurcated legs of the first latch member apart and press the elastomeric tube against the conductive pin with a force sufficient to hold the conductive pin in place against the electrical contact when the first and second latch members are squeezed together, and wherein the first and second radial flanges on the elastomeric tube establish a body fluid impervious seal between the first and second latch members and the device connector when the first and second latch members are squeezed together.

8. The lead terminal connector as in claim 7 wherein the first latch member includes a barb on each of the pair of bifurcated legs and the elastomeric tube includes a shoulder proximate one end thereof for receiving said barbs when the first and second latch members are squeezed together.

9. The lead terminal connector as in claim 7 wherein the first latch member comprises a generally flat head member with said pair of legs integrally formed therewith and extending generally perpendicularly therefrom.

10. The lead terminal connector as in claim 7 wherein said second latch member comprises a generally flat head member with said tapered wedge surface integrally formed therewith and extending generally perpendicularly therefrom.

11. The lead terminal connector as in claim 8 wherein said first latch member and said second latch member interlock with one another upon their being squeezed together.

12. The device connector-to-lead terminal connector as in claim 11 wherein, said radial flanges form a fluid impervious seal between then first and second side surfaces of the device connector and the first and second latch members when the first and second latch members are interlocked to one another.

* * * * *